United States Patent [19]

Nakamura et al.

[11] Patent Number: 5,871,916
[45] Date of Patent: *Feb. 16, 1999

[54] ECDN PROTEIN AND DNA ENCODING THE SAME

[75] Inventors: Yusuke Nakamura, Kanagawa; Hiroko Saito, Tokyo, both of Japan

[73] Assignees: Cancer Institute; Eisai Co., Ltd., both of Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 649,619

[22] PCT Filed: Sep. 21, 1995

[86] PCT No.: PCT/JP95/01909

§ 371 Date: May 2, 1996

§ 102(e) Date: May 2, 1996

[87] PCT Pub. No.: WO96/09324

PCT Pub. Date: Mar. 28, 1996

[30] Foreign Application Priority Data

Sep. 21, 1994 [JP] Japan .................................. 6-226270

[51] Int. Cl.$^6$ .............................. C12Q 1/68; C07H 21/02; C07H 21/04
[52] U.S. Cl. .......................... 435/6; 435/172.1; 536/23.1; 536/23.5; 536/24.3; 536/24.31; 536/24.33
[58] Field of Search .......................... 435/6, 69.1, 172.1, 435/172.3, 320.1; 536/23.1, 23.5, 24.3, 24.31, 24.33

[56] References Cited

FOREIGN PATENT DOCUMENTS

94/07916  4/1994  WIPO .
95/13373  5/1995  WIPO .

OTHER PUBLICATIONS

Sommer et al "Minimal homology requirements for PCR primers" *Nucleic Acids Research* vol. 17(16):6749, 1989.
Science, vol. 240 pp. 889–895, 1988.
Th EMBO Journal, vol. 11, No. 3, pp. 1003–1013, 1992.
Nature, vol. 355, pp. 359–361, 1992.
Faseb J., vol. 5, pp. 2243–2249, 1992.
Cell, vol. 67, pp. 59–77, 1991.
Gene, vol. 147, pp. 273–276, 1994.
Proc. Natl. Acad. Sci. USA, vol. 91, pp. 10809–10813, 1994.

*Primary Examiner*—George C. Elliott
*Assistant Examiner*—Sean McGarry
*Attorney, Agent, or Firm*—Flynn, Thiel, Boutell & Tanis, P.C.

[57] ABSTRACT

A DNA encoding a novel steroid hormone receptor-like protein was obtained from a human fetal lung cDNA library, and its structure was determined. Further, the protein encoded by the gene was isolated, identified, and designated as an ECDN protein. Furthermore, a protein encoded by a DNA lacking a part of the above gene was isolated, identified, and designated as an ECDN paucimolecular protein.

It was proven that the ECDN paucimolecular protein was expressed in various cancer cells. Therefore, it is expected that it becomes possible to diagnose and treat cancers by analyzing the expression of the ECDN protein and the ECDN paucimolecular protein in a subject tissue. Furthermore, attained to develop novel pharmaceuticals can be developed by finding natural and synthetic compounds capable of binding specifically to the ECDN protein and the ECDN paucimolecular protein.

5 Claims, 2 Drawing Sheets

ECDN PROTEIN AND DNA ENCODING THE SAME

BACKGROUND OF THE INVENTION

1. Field of the Invention

The present invention relates to an ECDN protein, which is a novel steroid hormone receptor-like protein, a DNA encoding the same and processes for the production and use of this protein.

2. Description of the Related Art

As steroid hormone receptor-like proteins, there have been found and identified a group of proteins which are homologous with each other in amino acid sequence. These proteins are respondent not only to steroid hormones but also to thyroid hormones and derivatives of fat-soluble vitamins such as vitamin D metabolites and natural and synthetic derivatives thereof, retinoic acid and natural and synthetic derivatives thereof and vitamin A metabolites. These ligand-dependent transcription regulating proteins constitute a superfamily and can regulate the expression of a specific gene by binding directly to a response element of a DNA specific for stimulation by a hormone or a ligand. It has been revealed that these receptor proteins play very important roles in the development, differentiation and the maintenance of homeostasis as transcription regulating factors which regulate the expression of specific genes with the use of hormones or vitamins as ligands [Evans, R. M., Science, 240, 889 (1988)]. Thus, natural and synthetic derivatives which are capable of binding to these receptor proteins and-acting as ligands have been widely studied and applied in the fields of medicine, pharmacology and agriculture.

A group of proteins seemingly belonging to the super-family of steroid hormone receptor proteins involve a group of a number of proteins which have been produced by molecular clonings effected by hybridizations under the lowered stringency, paying attention to the homology of DNA binding domains common to the superfamily. The group of these proteins include a group of proteins called orphan receptors, the ligands specific for which have been unidentified hitherto [Laudet, V. et. al., EMBO J., 11, 1003 (1992)]. It is considered that studies on the identification of the ligands specific for these orphan receptors and functions of these orphan receptors as transcription regulating factors are highly important, since novel medical and biological findings applicable to medicines and agriculture might be provided thereby. For example, it has been clarified that the ligand of retinoid X receptor (RXR), which was once regarded as an orphan receptor, is 9-cis-retinoic acid and that RXR is a receptor having an important role in transcriptional regulation [Levin, A., et. al., NATURE, 359 (1992)]. It seems that in the proteins participating in the human transcriptional regulation mechanism depending on ligands, a number of receptors still remain unidentified. Therefore, it is highly meaningful to isolate and identify these receptors from the viewpoint of the application thereof to medicine and pharmacology too.

DISCLOSURE OF THE INVENTION

SUMMARY OF THE INVENTION

It is an object of the present invention to provide a novel receptor protein originating from human beings which belongs to the steroid/thyroid hormone receptor superfamily, a gene encoding the protein, a process for analyzing the function of a receptor with the use of the protein and a process for searching a ligand with the use of the protein, thus broadening the application field thereof.

As the results of comparison of the structures of proteins in a group constituting the superfamily of steroid hormone receptor-like proteins and analyses of the functions with the use of mutated receptors constructed via gene modification, it has been clarified that these proteins in the group comprise functional domains. It has been clarified that a domain consisting of 66 to 68 amino acids and having 2 zinc fingers shows the highest homology among the proteins in the group belonging to the superfamily and binds to a DNA, while a domain consisting of about 250 amino acids on the C-terminal side participates in the ligand-dependency as a domain capable of binding to a ligand [Wahli, W. et. al., FASEB, J., 5, 2243 (1991)]. These steroid hormone receptor-like proteins have been detected and identified not only in mammals but also in insects. As a representative example thereof, a receptor to ecdysone, which is a steroid hormone controlling the metamorphoses of insects, is known as a member of the above-mentioned superfamily [Koelle, M. R. et. al., Cell, 67, 59 (1991)].

The present inventors randomly selected clones from a human fetal lung cDNA library and identified the nucleotide sequence on the 5'-terminal side of each clone. Then, the amino acid sequences deduced therefrom were subjected to a search. As a result, they found a clone having an amino acid sequence highly homologous with that of the ecdysone receptor which had been isolated and identified from an insect fat body. Since this clone included no full length cDNA, they screened cDNA libraries again with the use of this clone as a probe. Thus, they successfully obtained a clone including a full-length cDNA from a human mammary gland library. The amino acid sequence of the protein encoded by this cDNA was highly homologous with those of the ecdysone receptor, human and mouse retinoic acid receptors and thyroid hormone receptor. In a site seemingly corresponding to the DNA binding domain, in particular, a region including 2 zinc fingers was conserved with a high homology. It was also confirmed that a site corresponding to the ligand binding domain showed a high homology with those of the above-mentioned ecdysone receptor and retinoic acid receptor and had a domain structure characteristic to those of steroid hormone receptor-like proteins. Thus, it was proven that this protein was a novel member of the group of the steroid hormone receptor-like proteins which had never been reported so far. The present inventors designated this protein as "ECDN protein".

By introducing the CDNA encoding this receptor protein into a host (*Escherichia coli*, a yeast, insect cells, mammalian cells, etc.) to thereby prepare a transformant, the receptor protein of the present invention can be isolated and purified and thus the structure of the ligand binding thereto can be determined. Moreover, a novel synthetic ligand or a response element capable of-binding to this receptor can be screened by a binding test with the use of the purified protein. When the cDNA encoding this receptor protein is subjected to cotransformation together with a plasmid including a response element and a reporter gene, it becomes possible to examine the functions of this receptor on the transcriptional activity in detail.

The present invention is highly meaningful, since it enables the function of the above-mentioned protein as a transcription regulating factor to be analyzed by examining the interactions thereof with the DNA response element binding thereto and other transcription regulating factors and screening a ligand specific thereto, and to broaden the scope of investigations aiming at the development of novel pharmaceuticals and diagnostic and preventive drugs, thus bringing about a rapid progress in the discoveries in this field.

The present inventors prepared the anti-ECDN protein monoclonal antibody and analyzed the expression of this protein in various cells. As a result, it was surprisingly confirmed that, in addition to the ECDN protein of about 50 kDa, a paucimolecular protein of about 40 kDa was expressed specifically in cancer cells. Subsequently, the structure of this paucimolecular protein was identified. It was confirmed that this paucimolecular protein was a protein corresponding to the ECDN protein but was lacking in 97 amino acids, as a result of the deletion of 291 bases from the DNA encoding the ECDN protein. Thus, the present inventors designated this protein as "ECDN paucimolecular protein". From this fact, it is understood that the ECDN paucimolecular protein in accordance with the present invention is a unique protein which is widely applicable to, e.g., the diagnosis and treatment of cancers.

Thus, the present invention provides (1) an ECDN protein having an amino acid sequence which comprises the whole or a part of an amino acid sequence encoded by the nucleotide sequence described in sequence ID NO: 1; and (2) an ECDN paucimolecular protein having an amino acid sequence which comprises the whole or a part of an amino acid sequence encoded by the nucleotide sequence described in sequence ID NO: 2.

The present invention also includes an ECDN protein which is substantially equivalent to the ECDN protein having an amino acid sequence described in sequence ID NO: 1 and obtained by the addition or insertion of one or more amino acid residues to(into) the protein, or the deletion of or substitution for one or more consecutive amino acid residues in the protein. Such equivalent substances are included in the present invention, so long as it exerts similar effects in the studies and diagnoses of ECDN proteins. Furthermore, the present invention includes an ECDN paucimolecular protein which is substantially equivalent to the ECDN paucimolecular protein having an amino acid sequence described in sequence ID NO: 2 and obtained by the addition or insertion of one or more amino acid residues to(into) the protein, or the deletion of or substitution for one or more consecutive amino acid residues in the protein. Such equivalent substances are included in the present invention, so long as it exerts similar effects in the studies and diagnoses of ECDN paucimolecular proteins.

The present invention further provides (3) a DNA encoding an ECDN protein which has a nucleotide sequence comprising the whole or a part of the nucleotide sequence described in sequence ID NO: 1; and (4) a DNA encoding an ECDN paucimolecular protein which has a nucleotide sequence comprising the whole or a part of the nucleotide sequence described in sequence ID NO: 2.

Similar to the case of the above-mentioned ECDN protein, DNAs which are substantially equivalent to a DNA encoding an ECDN protein having the amino acid sequence described in sequence ID NO: 1 and obtained by the addition or insertion of one or more nucleotides to(into) the DNA, or the deletion of or substitution for one or more consecutive nucleotides in the DNA, i.e., equivalent substances, are also included in the present invention. Furthermore, similar to the case of the above-mentioned ECDN paucimolecular protein, DNAs which are substantially equivalent to a DNA encoding an ECDN paucimolecular protein having the amino acid sequence described in sequence ID NO: 2 and obtained by the addition or insertion of one or more nucleotides to(into) the DNA, or the deletion of or substitution for one or more consecutive nucleotides in the DNA, i.e., equivalent substances, are also included in the present invention.

The present invention furthermore provides (5) a vector comprising the above-mentioned DNA; (6) a transformant carrying this vector; and (7) a process for producing an ECDN protein or an ECDN paucimolecular protein which comprises culturing the transformant carrying the above-mentioned vector transfected thereinto and recovering an expression product thereof.

In addition, the present invention provides (8) a cotransformant carrying, transfected thereinto, a vector comprising a DNA encoding an ECDN protein and a reporter vector comprising a DNA respondent to the vector; (9) a cotransformant carrying, transfected thereinto, a vector which comprises a DNA encoding a chimeric ECDN protein obtained by replacing the DNA binding domain of an ECDN protein with the DNA binding domain of a known steroid hormone receptor-like protein other than an ECDN protein and a reporter vector comprising a DNA respondent to the vector; (10) a process for screening a compound capable of acting on the above-mentioned cotransformant which comprises using the cotransformant; and (11) a process for screening a compound capable of binding to the above-mentioned ECDN protein which comprises using the ECDN protein.

The present invention provides (12) a DNA probe which has a nucleotide sequence comprising the whole or a part of the nucleotide sequence described in sequence ID NO: 1 or 2; (13) a DNA primer which has a nucleotide sequence comprising a part of the nucleotide sequence described in sequence ID NO: 1 or 2; (14) a process for analyzing a gene of an ECDN protein or an ECDN paucimolecular protein which comprises hybridizing the above-mentioned DNA probe or the above-mentioned DNA primer with a subject DNA; (15) a process for testing cells which comprises assaying a mRNA of an ECDN protein or an ECDN paucimolecular protein in a subject tissue or subject cells by using the above-mentioned DNA probe or the above-mentioned DNA primer; (16) a process for testing cells which comprises hybridizing the above-mentioned DNA probe with a subject DNA to thereby assay a gene of an ECDN protein or an ECDN paucimolecular protein; (17) a process for testing cells which comprises amplifying a subject mRNA by the RT-PCR method with the use of the above-mentioned DNA primer and assaying the expression of a gene of an ECDN protein or an ECDN paucimolecular protein; and (18) a process for testing cells which comprises amplifying a subject mRNA by the RT-PCR method with the use of the DNA primer described in sequence ID NO: 6 and the DNA primer described in sequence ID NO: 7 and assaying the expression of a gene of an ECDN protein or an ECDN paucimolecular protein.

The present invention further provides (19) a polyclonal antibody or a monoclonal antibody capable of binding to an ECDN protein or an ECDN paucimolecular protein; (20) a process for immunochemically assaying an ECDN protein or an ECDN paucimolecular protein which comprises using the above-mentioned polyclonal antibody or monoclonal antibody; (21) a process for testing cells which comprises immunohistochemically staining a subject tissue or subject cells with the use of the above-mentioned polyclonal antibody or monoclonal antibody and determining the intracellular distribution of an ECDN protein or an ECDN paucimolecular protein; and (22) a process for testing cells which comprises determining the amount of an ECDN protein or an ECDN paucimolecular protein expressed in a subject tissue or subject cells by using the above-mentioned polyclonal antibody or monoclonal antibody.

The present invention furthermore provides (23) a peptide comprising at least eight consecutive amino acids in an amino acid sequence that an ECDN protein has; and (24) a peptide comprising at least eight consecutive amino acids in an amino acid sequence that an ECDN paucimolecular protein has.

In addition, the present invention provides (25) an antisense DNA or an antisense RNA hybridizable specifically with a mRNA of an ECDN paucimolecular protein; (26) a ribozyme capable of cleaving specifically a mRNA of an ECDN paucimolecular protein; and (27) a pharmaceutical for gene therapy which comprises, as the active component, a gene construction capable of expressing the above-mentioned antisense DNA, the above-mentioned antisense RNA or the above-mentioned ribozyme.

The present invention also includes (1) a protein comprising the one including the whole or a part of the protein represented by sequence ID NO: 1; (2) a DNA comprising the one including the whole or a part of the DNA represented by sequence ID NO: 1; (3) a plasmid including the whole or a part of the DNA described in sequence ID NO: 1, and a transformant carrying the same; (4) a process for producing the protein represented by sequence ID NO: 1; (5) an antibody which binds to the protein represented by sequence ID NO: 1; (6) a primer or a probe including a part of the DNA sequence represented by sequence ID NO: 1, and a process for analyzing a gene characterized by using the same; (7) a process for analyzing a binding ligand or a response DNA with the use of the whole or a part of the protein represented by sequence ID NO: 1; and (8) a process for analyzing a transcription regulating function with the use of a cotransformant transformed with both an expression vector including the whole or a part of the DNA sequence represented by sequence ID NO: 1 and a reporter plasmid which has been constructed in order to observe the promotion or suppression of the expression of a reporter gene in response to the protein described in sequence ID NO: 1. In this case as well, the above-mentioned protein and DNA also include those substantially equivalent thereto.

The DNA of the present invention and a DNA complementary to said DNA are applicable to an analysis of the gene of the ECDN protein or the ECDN paucimolecular protein, or an analysis of the expression of said gene, by using a part thereof as a primer or probe. The term "a part of the DNA" as used herein refers to a sequence of at least eight consecutives nucleotides, preferably at least ten nucleotides, still more preferably at least fifteen to twenty-five nucleotides corresponding to (i.e., contained in or complementary to) the nucleotide sequence of the DNA according to the present invention. The primer or probe of the present invention which is an oligonucleotide or polynucleotide may contain also at least one nucleotide(s) not corresponding to the nucleotide sequence of the DNA encoding the ECDN protein or the ECDN paucimolecular protein.

The protein of the present invention is applicable to an antibody preparation and agents for study and diagnosis containing such an antibody, by the use of the whole or a part thereof as an epitope. The term "epitope" refers an antigenic determinant of a polypeptide. It is well known that the epitope is generally composed of at least six amino acid residues and that a polypeptide composed of six amino acid residues combines with an antibody [see WO of PCT Patent Applications No. 8403564, published on Sep. 13, 1984 (Applicant: COMMONWEALTH SERUM LABS AND GEYSEN, H.M.)]. The term "a part of the protein" as used herein refers to a polypeptide comprising at least six consecutive amino acid residues, preferably at least eight consecutive amino acid residues, still more preferably at least about ten consecutive amino acid residues, and particularly preferably at least about fifteen to twenty-five consecutive amino acid residues, on the basis of the amino acid sequence of the protein of the present invention. The above-mentioned polypeptide may contain also at least one amino acid residue (s) not corresponding to the amino acid sequence of the ECDN protein or the ECDN paucimolecular protein.

Now, the present invention will be described in detail.

DETAILED DESCRIPTION OF THE INVENTION

(1) Isolation of cDNA Clone cDNAs are synthesized on the basis of human fetal lung mRNAs in a conventional manner and a cDNA library having cDNA inserts cloned in a definite orientation is prepared. Clones are randomly selected from this library and the nucleotide sequence of each clone is partially determined from the 5'-terminal side. Thus, a clone having a nucleotide sequence which is homologous with that of an ecdysone receptor cloned from a mosquito fat body tissue is selected. When the clone thus selected does not include the full-length cDNA, various cDNA libraries are screened by using the cDNA of this clone as a probe to thereby give the target clone including the full-length cDNA.

(2) Identification of the Full Structure of the Gene

It has been confirmed that the cDNA obtained by the above method is a novel DNA sequence described in sequence ID NO: 1. The present inventors designated the novel protein having an amino acid sequence encoded thereby as an ECDN protein.

Similarly, the present inventors obtained a cDNA having a novel DNA sequence described in sequence ID NO: 2, and designated the novel protein having an amino acid sequence encoded thereby as an ECDN paucimolecular protein.

(3) Recombinant Expression Vector and Transformant Thereof

Although illustration in accordance with the ECDN protein will be conducted herein, the same will be applicable to the ECDN paucimolecular protein.

The DNA encoding the human ECDN protein obtained by the above-mentioned method or a fragment thereof is inserted into an appropriate vector. Then this vector is transfected into suitable host cells. Thus a transformant can be obtained. When this transformant is cultured in a conventional manner, the human ECDN protein can be produced in a large amount from the culture. More particularly, the DNA encoding the human ECDN protein or a fragment thereof is religated to a vector suitable for the expression thereof downstream of a promoter according to the customary procedure with the use of restriction enzymes and DNA ligase. Thus, a recombinant expression vector can be constructed. Examples of the vector usable include plasmids pBR322 and pUC18 derived from *Escherichia coli,* plasmid pUB110 derived from *Bacillus subtilis,* plasmid pRB15 derived from a yeast, bacteriophage vectors λgt10 and λtg11, and vector SV40. The vectors are not particularly limited as long as they can be replicated or amplified in the host. The promoter and terminator are also not particularly limited as long as they suit the host employed in the expression of the DNA sequence encoding the human ECDN protein. Appropriate members thereof can be used in combination in accordance with the host. The DNA to be employed is not limited to the one having the DNA sequence described in sequence ID NO: 1, as long as it encodes the human ECDN protein. Use may be made of a DNA having a DNA sequence resulting from intentional or unintentional substitution, deletion, insertion and/or addition conducted individually or in combination at a part of the DNA sequence of sequence ID NO: 1. Further, use may be made of one chemically synthesized.

The recombinant expression vector thus obtained is introduced into the host by, for example, the competent cell method [J. Mol. Biol., 53, 154 (1970)], the protoplast method [Proc. Natl. Acad. Sci. USA, 75, 1929 (1978)], the calcium phosphate method [Science, 221, 551 (1983)], the in vitro packaging method [Proc. Natl. Acad. Sci. USA, 72, 581 (1975)] or the virus vector method [Cell, 37, 1053 (1984)] to thereby give a transformant. As the host, use can be made of any of *Escherichia coli, Bacillus subtilis,* yeasts, insect cells, animal cells and the like. The transformant thus obtained is cultured in a medium appropriately selected depending on the host. The culturing is usually effected at a temperature of from 20° to 45° C. within a pH ranging from 5 to 8, optionally under aeration and/or stirring. The transformation to be effected is not restricted to the one with only a recombinant expression vector of the ECDN protein according to the present invention. That is to say, it is possible to form a cotransformant by using a reporter plasmid including a DNA response element capable of binding to the ECDN protein, with the ECDN protein.

(4) Separation and Purification of Recombinant Protein

The separation of the ECDN protein or the ECDN paucimolecular protein from the culture and its purification may be conducted by an appropriate combination of conventional separation and purification methods. As these conventional methods, for example, salting out, solvent precipitation, dialysis and gel filtration, electrophoresis, ion exchange chromatography, affinity chromatography, and reversed-phase high-performance liquid chromatography are cited.

(5) Preparation of Antibody

An antibody can be prepared by the conventional method with the use of all or a part of the ECDN protein as an antigen. For example, a polyclonal antibody may be prepared by giving a plurality of subcutaneous, intramuscular, intraperitoneal or intravenous inoculations of the antigen to an animal such as a mouse, a guinea-pig and a rabbit to thereby satisfactorily immunize the same, collecting the blood specimen from the animal, and performing serum separation. In this procedure, commercially available adjuvants can be used.

A monoclonal antibody may be prepared by, for example, conducting the fusion of splenocytes of a mouse immunized with the ECDN protein with commercially available mouse myeloma cells to thereby prepare a hybridoma and either culturing the hybridoma followed by separation of the antibody from the resultant supernatant or administering the hybridoma to a mouse followed by separation of the antibody from the mouse ascites.

It is not always necessary that the ECDN protein to be used as the antigen has the whole amino acid structure. Namely, use may be made of a peptide having a partial structure of the protein, a variant or derivative of the protein, or a fusion peptide resulting from fusion with another peptide. The method for preparing these is not critical and it may be biological or chemosynthetic.

According to the similar method to that described above, antibodies against the ECDN paucimolecular protein can also be prepared. When the ECDN protein and the ECDN paucimolecular protein are analyzed individually, it is preferable to suitably select the portion to be used as an epitope from a portion not present in the ECDN paucimolecular protein, a portion newly formed in the ECDN paucimolecular protein or the other portion.

The obtained antibody enables the identification and quantity determination of the ECDN protein and/or the ECDN paucimolecular protein in human biospecimens and can be used in, for example, various agents. The antibody of the present invention can be used also in the form of a fragment thereof, e.g., $F(ab')_2$, Fab' or Fab, or a derivative thereof, if necessary. Further, the antibody of the present invention is applicable also as a chimera antibody, a humanized antibody or a human antibody. All of these fragments and antibodies are included in the conception of the present invention.

The immunoassay of the ECDN protein or the ECDN paucimolecular protein may be conducted in accordance with the generally known procedure and can be executed by, for example, any of the fluorescent antibody technique, passive agglutination and enzyme antibody technique.

(6) Analysis of Gene and Expression Thereof

Any mutation of a gene encoding the ECDN protein or the ECDN paucimolecular protein according to the present invention can be analyzed by the use of a probe comprising a restriction enzyme fragment of the DNA encoding the protein or by the use of, as a primer, an oligonucleotide obtained by appropriately selecting a suitably positioned nucleotide sequence from the DNA encoding the protein and synthesizing therewith.

Also, any abnormality such as insertion and deletion in the gene as a specimen can be detected by the above analysis.

*Escherichia coli* DH5α/pFATSR, which carries a plasmid including the DNA encoding this ECDN protein, has been deposited at National Institute of Bioscience and Human-Technology, Agency of Industrial Science and Technology, Ministry of International Trade and Industry under the accession number FERM BP-4769 on Aug. 4, 1994.

(7) Analyses of Substance Binding to ECDN Protein and Response DNA

Although illustration in accordance with the ECDN protein will be conducted herein, the same will be applicable to the ECDN paucimolecular protein.

The transformant prepared in the above (3) and capable of expressing the ECDN protein is cultured for a definite period of time. Then the ECDN protein expressed from the transformant cells is separated and recovered. The structure of the ligand binding to the fraction containing the ECDN protein under the culture conditions can be determined by combining customary procedures such as extraction, HPLC, mass spectrometry and nuclear magnetic resonance spectrometry. After clarifying the structure of the ligand, a receptor binding test is effected by using the crude extract obtained from the transformant or the ECDN protein, which has been isolated and purified, together with labeled ligands. Thus, natural or synthetic derivatives capable of binding to the ECDN protein can be screened.

The response DNA to which the ECDN protein binds can be analyzed by a customary DNA binding test such as the gel shift method with the use of the crude extract obtained from the transformant or the ECDN protein, which has been isolated and purified, together with an oligonucleotide labeled with an isotope or a nonisotopic substance such as biotin.

(8) Analysis of Transcription Regulating Function by Using a Cotransformant with Reporter Plasmid Although illustration in accordance with the ECDN protein will be conducted herein, the same will be applicable to the ECDN paucimolecular protein.

A DNA sequence to which the ECDN protein or known steroid hormone receptor-like protein analogous bind is inserted into, e.g., a promoter derived from SV40 or cytomegalovirus or an expression promoter of a yeast upstream, while a reporter gene of, for example, chloramphenicol acetyltransferase, placental alkaline phosphatase, luciferase or LacZ is inserted into the promoter downstream to thereby construct a reporter plasmid. An ECDN protein expression vector or an expression vector of a chimera ECDN protein obtained by substituting a DNA binding domain of a known steroid hormone receptor-like protein for the DNA binding domain of the ECDN protein is transfected into a yeast, insect cells or animal cells together with the reporter plasmid or an expression vector of another steroid hormone receptor-like protein to thereby give a cotransformant. In the case of the ECDN protein expressed in such a transformant, the ECDN protein per se or its complex interacts with another receptor protein expressed simultaneously or a protein in the cells and thus binds to the reporter plasmid, thus affecting the transcription of the reporter gene. The expression of the reporter gene product via the transcription of the reporter gene can be detected through a reaction specific for the reporter gene product. Such a method for analyzing the ability to regulate transcription makes it possible, for example, to screen a substance having a transcription regulating function via the ECDN protein.

(9) Expression of ECDN Paucimolecular Protein in Cancer Cells

As will be shown in Example 9 and thereafter, the present inventors analyze various cancer cell lines and cancer tissues by the Western blotting method and the RT-PCR method with the use of anti-ECDN antibodies and, as a result, find that an ECDN paucimolecular protein of about 40 kDa is cancer-specifically expressed in various cancer cell lines and cancer tissues. The nucleotide sequence of the DNA encoding this ECDN paucimolecular protein is identified and, as the result, it is revealed that this nucleotide sequence is one described in sequence ID NO: 1 but lacking in a part ranging from the base Nos. 387 to 677 thereof. Further, it is also confirmed that this ECDN paucimolecular protein is accumulated in the nucleoli of the cells by immunohistological staining.

These facts suggest that an extremely closely correlation is present between the progression of cancer and the formation of the ECDN paucimolecular proteines. Therefore, it becomes possible to distinguish normal cells from cancer cells by analyzing the genes of an ECDN protein and an ECDN paucimolecular protein and intracellular distribution thereof in subject cells or subject tissues.

The gene analysis is conducted by assaying a DNA or mRNA in a subject tissue with the use of a probe or a primer which has a DNA sequence comprising a part of the nucleotide sequence of the DNA encoding an ECDN protein or an ECDN paucimolecular protein. The DNA sequence of the probe or the primer can be appropriately selected depending on the purpose by considering the region which is deleted in the ECDN paucimolecular protein in the nucleotide sequence of the DNA encoding the ECDN protein. The assay of the DNA or mRNA in the subject tissue can be conducted in accordance with a known method.

It is also possible to use an antibody in the assay of the ECDN protein and the ECDN paucimolecular protein. An antigen (epitope) for the preparation of the antibody may be appropriately selected from among a part common to both proteins, a site deleted in the ECDN paucimolecular protein, a binding site of the ECDN paucimolecular protein after the deletion (a part including the neighborhood of the amino acid No. 61 described in sequence ID NO: 2), etc. It is also possible to select an antibody suitable for the occasion from among those prepared by using such sites each as an antigen.

(10) Application to Medicine

It is expected to be found a substance, from among the substances acting on the regulation of the transcription via an ECDN protein, which stimulates the normal function of the ECDN protein to thereby introduce the differentiation of tumor cells wherein an ECDN paucimolecular protein is expressed into normal cells or which suppresses the abnormal multiplication of the tumor cells, as all-trans retinoic acid in the case of promyelocyte leukemia.

It is also expected that the abnormal multiplication of tumor cells could be suppressed by suppressing the expression of the ECDN paucimolecular protein in a tumor with the use of an antisense nucleic acid (DNA or RNA) hybridizable specifically with the mRNA of the ECDN paucimolecular protein or a ribozyme. It is furthermore expected that similar effects could be established by introducing a gene construction capable of expressing an antisense RNA hybridizable specifically with the mRNA of the ECDN paucimolecular protein or a ribozyme into a tumor. As the site of the mRNA of the ECDN paucimolecular protein at which another substance (antisense RNA or ribozyme) specifically hybridizes, a site at which bases are deleted in the nucleotide sequence of the ECDN protein followed by binding, namely, a part including the neighborhood of the base No. 387 in the nucleotide sequence encoding the ECDN paucimolecular protein described in sequence ID NO: 2.

A substance suppressing the expression of the ECDN paucimolecular protein, which cannot be observed in any normal tissue, can be screened by detecting the expression of the mRNA of the ECDN protein or the ECDN paucimolecular protein with the use of an appropriate primer, probe or antibody.

It is expected that novel pharmaceuticals for treatment, diagnostic drugs and preventive drugs are invented by analyzing the function of the human ECDN protein of the present invention of regulating transcription and a gene per se encoding this protein with the use of the human ECDN protein or a DNA, which includes the whole or a part of the DNA encoding this protein, and thus analyzing natural and synthetic compounds capable of binding specifically to this receptor protein. Moreover, it is expected that the detection of the expression of the ECDN protein and the ECDN paucimolecular protein in a subject tissue and the analyses on the genes of the ECDN protein and the ECDN paucimolecular protein are applicable to the diagnosis and treatment of cancer.

EXAMPLES

Figure 1:
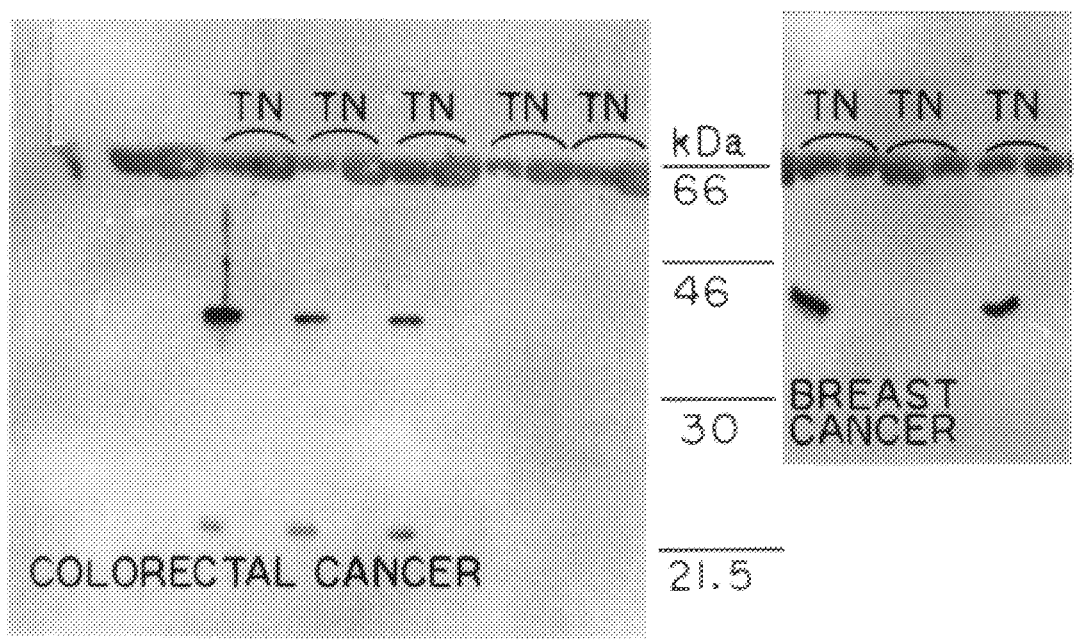
FIG. 1 shows the results of the Western blotting on a colorectal cancer tissue and a breast cancer tissue (T) and normal tissues (N) corresponding respectively thereto with the use of the anti-ECDN protein monoclonal antibody.

The following Examples will be given in detail and specifically to further illustrate the present invention, and not by way of limiting the present invnetion.

(Example 1) Preparation of Human cDNA Library cDNAs were synthesized on the basis of human fetal lung and mammary gland mRNAs (purchased from Clontech) and cDNA libraries each having cDNA inserts, which had been cloned in a definite orientation, were prepared with the use of a Uni-ZAP XR vector kit (purchased from Stratagene).

(Example 2) Selection of Clone

Clones were randomly selected from the human fetal lung cDNA library prepared in the above Example 1 and the nucleotide sequence of each clone was partially determined from the 5'-terminal side. When these nucleotide sequences were compared with known ones in a data base with the use of the FASTA algorithm, a clone L1-1793 having a nucleotide sequence which was homologous with that of the insect ecdysone receptor was found out.

(Example 3) Cloning of Full-Length cDNA

Since the clone L1-1793 was not a full-length clone, the cDNA insert of the clone L1-1793 was labeled with $^{32}$P by the random prime labeling method [Feinberg et al., Anal. Biochem., 132, 6 (1983)] and used as a probe in the screening of various cDNA libraries by the hybridization method. As a result, a clone including the full-length cDNA was obtained from a human mammary gland cDNA library. As a result of the analysis of the structure of this clone, it was confirmed that this clone had a novel DNA nucleotide sequence consisting of 1,979 bp involving a 5'-noncoding region of 205 bp, a coding region of 1,386 bp and a 3'-noncoding region of 388 bp (see sequence ID NO: 1). The open reading frame involved in the sequence of this cDNA encoded a novel protein (ECDN protein, see sequence ID NO: 1) consisting of 461 amino acids.

(Example 4) Expression of Gene Encoding ECDN Protein in Various Human Tissues

The DNA insert of the cDNA clone (see sequence ID NO: 1) obtained in the above Example 3 was labeled with $^{32}$P and employed as a probe in the Northern blot analyses of various human tissue mRNAs (the kit for Northern blot analysis was purchased from Clontech). As a result, expression was recognized in the form of a mRNA band having a size of about 2 kb in all the studied tissues, i.e., brain, heart, kidney, liver, lung, pancreas, placenta, skeletal muscle, large intestine, peripheral leukocyte, ovary, prostate, small intestine, spleen, testicle and thymus gland.

(Example 5) Structural features of ECDN protein

The ECDN protein having the amino acid sequence described in sequence ID NO: 1, which has been deduced from the open reading frame corresponding to the sequence ranging from the base No. 206 to the base No. 1,591 of the nucleotide sequence described in sequence ID NO: 1, is a novel protein consisting of 461 amino acids. The amino acid sequence ranging from the residue No. 87 to the residue No. 152 (i.e., 66 residues) conserves 2 zinc fingers characteristic to a group of steroid hormone receptor-like proteins and is highly homologous with the sequences of DNA binding domains of receptor proteins, such as ecdysone receptor, retinoic acid receptor and thyroid hormone receptor. In the amino acid sequence, 219 residues ranging from the amino acid No. 243 to the amino acid No. 461 at the C-terminus is highly homologous with the sequences of ligand binding domains located on the C-terminal side of ecdysone receptor and retinoic acid receptor, and corresponds to the ligand binding site of this protein.

(Example 6) Construction of Recombinant ECDN Protein Expression Vector

By using a cDNA including the nucleotide sequence encoding the ECDN protein described in sequence ID NO: 1 as a template, a partial sequence including its protein-coding region was amplified by the PCR method. The following sequences were selected for the primers.

Primer 1: 5'-GACGGATCCATGTCCTCTCCTACCA CGAGTT-3' (a coding strand, corresponding to a sequence ranging from the base No. 206 to the base No. 227 in sequence ID NO: 1, described in sequence ID NO:3).

Primer 2: 5'-CTAGAATTCGGAGGGTGGTCAGGCA AGGC-3' (an antisense strand, corresponding to an antisense strand ranging from the base No. 1,634 to the base No. 1,615 in sequence ID NO: 1 in the reverse orientation, described in sequence ID NO: 4).

Primer 1 has a BamHI cleavage site, added thereto, at the 5'-terminus, while primer 2 has an EcoRI cleavage site, added thereto, at the 5'-terminus. The PCR product was digested with BamHI and EcoRI. The resultant fragment was inserted into expression vector pGEX-2T (purchased from Pharmacia) preliminaly digested with BamHI and EcoRI, thereby constructing expression plasmid PGST-FATSR. *E. coli* DH5α was transformed with the plasmid pGST-FATSR and resulting transformants were selected based on the ampicillin resistance, thereby obtaining a transformant capable of expressing a fusion protein of glutathione-S-transferase and ECDN protein.

(Example 7) Expression of Recombinant ECDN Protein and its Purification

The transformant obtained in Example 6 was cultured, and the recombinant ECDN fusion protein was extracted from the resultant culture and purified.

Specifically, the transformant was cultured by shaking the same in 100 ml of LB medium (1% peptone, 0.5% yeast extract and 1% NaCl) at 37° C. overnight. The resultant liquid culture was diluted 10-fold with LB medium pre-heated to 37° C. and the resulting dilution was further cultured at 37° C. for 30 to 90 minutes, thereby obtaining a culture of logarithmic growth phase. Isopropyl β-D-thiogalactopyranoside was added to 1 L of the culture so that the final concentration thereof became 1 mM, followed by culturing for 3 to 4 hours. The culture was centrifuged to thereby separate bacterial cells. 10 ml of a column buffer (150 mM NaCl, 16 mM $Na_2HPO_4$ and 4mM $NaH_2PO_4$, pH 7.3) was added to bacterial cells transformed with the expression vector PGST-FATSR, followed by sonication. A soluble fraction of a supernatant resulting from the cell disruption was applied to a glutathione-Sepharose 4B column (purchased from Pharmacia). The column was washed with the column buffer and then elution was conducted with an eluent containing 5 mM reduced glutathione. The eluted fraction was analyzed and fractionated by SDS polyacrylamide electrophoresis. As a result, a fraction in which the desired GST fusion protein of about 75 kDa was detected as a main band was obtained from the transformant constructed with the plasmid pGST-FATSR.

(Example 8) Preparation of Monoclonal Antibody and Polyclonal Antibody

The recombinant GST fused protein obtained in Example 7 was employed as an immune antigen, an antigen for purifying and screening antibodies and a standard antigen for assaying.

The anti-ECDN protein specific monoclonal antibody was prepared by immunizing a mouse with the GST fused protein. Namely, a solution of the GST fused protein in PBS (concentration: 500–1,000 μg/ml) was mixed with the complete adjuvant at a ratio of 1:1. The mixture thus obtained was intraperitoneally administered to mice in a dose of 100 μg/animal thrice at intervals of two weeks to thereby immunize the mice. After the completion of the immunization, hybridomas of P3U1 cells with the B cells of the mice were prepared by using PEG-15,000. These hybridomas were cultured and the antibody titer in the culture supernatant was monitored. Thus hybridomas capable of producing the anti-ECDN protein specific antibody were selected.

The determination of the antibody titer was conducted as follows: Specifically, first, the GST fused protein (1 μg/ml) obtained in Example 7 was immobilized on a polystyrene cup. Into this cup was introduced 100 μl of the culture supernatant to thereby effect the first reaction. The cup was washed and then antimouse IgG-HRP (horse-radish peroxidase) was introduced into the cup to thereby effect the second reaction. The cup was washed and then an enzyme substrate solution [a mixture of an aqueous solution of hydrogen peroxide with ABTS (2,2 '-azino-bis(3-ethylbenzothiazoline-6-sulfonic acid)] was introduced into the cup to thereby effect a color development reaction (the third reaction), which had been monitored.

The hybridomas selected were cultured in a 96-well multiplate, and then subjected to the HAT screening. About two weeks after the initiation of the culture, the antibody titer of the culture supernatant was determined to thereby select a clone capable of producing an antibody reacting specifically with the antigen. Cloning was further effected, and a clone (F1D5) was established as hybridomas capable of producing the antibody.

Each of 3×10$^6$ hybridomas thus obtained was intraperitoneally inoculated into a BALB/c mouse to which 0.5 ml of pristane had been intraperitoneally administered about 1 week before the inoculation. Eight to ten days after the inoculation, the ascites fluids were taken up. An antibody was purified from each ascites fluid by affinity chromatography with the use of a protein G column.

The preparation of a polyclonal antibody was conducted as follows: A sequence ranging from the amino acid No. 245 to the amino acid No. 260 was selected from the amino acid sequence of the ECDN protein described in sequence ID NO: 1. A peptide having the sequence thus selected was chemically synthesized and referred to as an antigen (sequence ID NO: 5). A complex of this antigen with Key Halle Limpet was prepared. Then, the complex was inoculated together with the complete adjuvant into a footpad of a rabbit four times at intervals of about two weeks to immunize the animal. Thus, an antibody was prepared. The antibody titer of the serum collected at each stage of the immunization was determined by the ELISA method. That is, the rabbit serum was introduced into a microplate coated with the antigen peptide and then reacted with the antigen peptide at room temperature for two hours. After washing the microplate, a goat anti-rabbit IgG antibody labeled with horse-radish peroxidase was added thereto. After reacting at room temperature for one hour and washing, an enzyme substrate solution was added to induce color development. Then the absorbance ($A_{405-490}$) was measured. As a result, five antiserum lots each showing an absorbance of 0.097 to 0.398 when used a 10,000-fold dilution of the serum were obtained (Example 9) Western Blotting By using the monoclonal antibody prepared in Example 8, the manner of existing of the ECDN protein in various tissues were analyzed by the Western blotting method in accordance with the conventional manner.

As a result, a normal ECDN protein of about 50 kilodalton (kDa) was observed in a normal tissue, while the over expression of an ECDN paucimolecular protein of about 40 kDa was observed in a colorectal cancer cell line, an esophageal cancer cell line and the HeLa cell line. Subsequently, the expressions of the ECDN protein and the ECDN paucimolecular protein were examined similarly by using breast cancer tissues, colorectal cancer tissues and normal tissues of the patients therewith. As a result, there were observed that the ECDN paucimolecular protein of about 40 kDa was expressed specific for cancer tissue in three colorectal cancer cases among seven cases and six breast cancer cases among nine cases, and that the expression of the normal ECDN protein lessened in these cancer tissues (see FIG. 1).

These results suggest that the ECDN paucimolecular protein with a low molecular weight is formed as the cancer proceeds, and therefore indicate that the detection of this abnormal protein (the ECDN paucimolecular protein) is applicable to the examination of cancer cells.

(Example 10) RT-PCR Experiment

To study the mechanism of the formation of such the ECDN paucimolecular protein, mRNAs were isolated from five colorectal cancer cell lines, six esophageal cancer cell lines and normal tissues, and an RT-PCR experiment was conducted.

Figure 2:
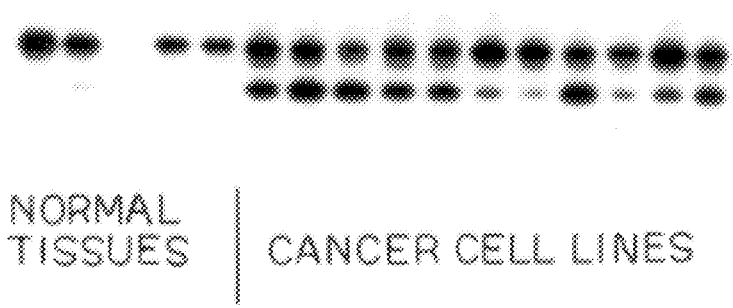
FIG. 2 shows the results of the RT-PCR on mRNAs of a normal tissue and a cancer cell line, respectively. In the RT-PCR, use was made of primers having nucleotide sequences described in sequence ID NO: 6 and sequence ID NO: 7, respectively.

From mRNAs, single-strand cDNAs were prepared in a conventional manner. Three segments of which the coding regions overlapped one another were amplified by the PCR method with the use of three paris of primers (the sequences described in sequence ID NOs: 6 and 7, the sequences described in sequence ID NOs: 8 and 9, and the sequences described in sequence ID NOs: 10 and 11, respectively; when expressed in base Nos. as described in sequence ID NO: 1, sequence ID NO: 6 corresponds to a sense DNA of the base No. 206 to the base No. 227, sequence ID NO: 7 corresponds to an antisense DNA of the base No. 733 to the base No. 753, sequence ID NO: 8 corresponds to a sense DNA of the base No. 700 to the base No. 725, sequence ID NO: 9 corresponds to an antisense DNA of the base No. 1226 to the base No. 1244, sequence ID NO: 10 corresponds to a sense DNA of the base No. 1205 to the base No. 1226, and sequence ID NO: 11 corresponds to an antisense DNA of the base No. 1615 to the base No. 1634). As a result, none of the amplification products of the segments on the 5'-termial side and those on the 3'-terminal side originating from the cancer cell lines showed any difference in size, when compared with the amplification products originating from the normal tissues. However, when the center segments were amplified, in addition to the amplification product having a normal size, an amplification product having a shorter size which was never observed in amplification products originating from normal tissues, was observed in all of the 11 cancer cell lines (see FIG. 2).

When the DNA sequence of this shorter amplification product was identified, it was proved that the 291 bases in the seventh exon (a portion corresponding to the base No. 387 to the base No. 677 in sequence ID NO: 1) in the DNA encoding the ECDN protein were deleted to be shortened. From this result, it was assumed that the variant mRNA specific for cancer cells would encode a protein of about 40 kDa in which 97 amino acids in the DNA binding domain were deleted. It is expected from such the fact that cancer cells can be detected by detecting the above-mentioned variant mRNA by using a manner such as the RT-PCR method and the hybridization method.

(Example 11) Immunohistochemical Analysis

By comparing the result of the RT-PCR experiment with the result of the Western blotting, it was estimated that the ECDN paucimolecular protein lacking in the DNA binding domain would be accumulated in a caner cell line. To examine whether this abnormal protein existed in the cytoplasm or the nucleus, various cell lines were immunologically stained with the use of the monoclonal antibody.

As a result, staining was slightly observed over the whole of cells in normal tissues. In contrast, it was obtained such a result that the accumulation of a protein binding to the anti-ECDN antibody in a large amount in nucleoli was suggested. Since the results of the Western blotting in Example 9 clearly indicated that a large amount of the ECDN paucimolecular protein of about 40 kDa was expressed in cancer cell lines, it was assumed that the protein accumulated in the nucleoli might be the ECDN paucimolecular protein. Based on those described above, it is expected that the decision whether they are cancer cells or normal cells can be conducted by examining the accumulation of an abnormal protein (an ECDN paucimolecular protein) in nucleoli with the use of an antibody.

We claim:

1. A method for assaying a cancer selected from the group consisting of a colorectal cancer and an esophageal cancer which comprises isolating an mRNA from a subject tissue or subject cells, amplifying the mRNA by the RT-PCR method with the use of a DNA primer which has a nucleotide sequence comprising at least eight consecutive nucleotides of the nucleotide sequence described in sequence ID NO: 2 and determining if a DNA is present which codes for the pauci-molecular ECDN protein.

2. The method of claim 1, wherein said nucleotide sequence comprises at least ten consecutive nucleotides of the nucleotide sequence described in sequence ID NO: 2.

3. The method of claim 1, wherein said nucleotide sequence comprises at least fifteen consecutive nucleotides of the nucleotide sequence described in sequence ID NO: 2.

4. The method of claim 1, wherein said nucleotide sequence comprises at least twenty-five consecutive nucleotides of the nucleotide sequence described in sequence ID NO: 2.

5. The method of claim 1, wherein said nucleotide sequence is sequence ID NO: 2.

* * * * *

SEQUENCE LISTING ( 1 ) GENERAL INFORMATION:

( i i i ) NUMBER OF SEQUENCES: 11

( 2 ) INFORMATION FOR SEQ ID NO: 1:

( i ) SEQUENCE CHARACTERISTICS:
        ( A ) LENGTH: 1979
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: Homosapiens ( v i i ) IMMEDIATE SOURCE:
        ( A ) LIBRARY: Human mammary gland cDNA
            library ( i x ) FEATURE:
        ( A ) NAME/KEY: CDS
        ( B ) LOCATION: 206..1591
        ( C ) IDENTIFICATION METHOD: experimental examination ( x i ) SEQUENCE DESCRIPTION: SEQ ID NO: 1:

```
TTTTGAGGGT   ATTTGAGTAG   CGGCGGTGTG   TCAGGGGCTA   AAGAGGAGGA   CGAAGAAAAG        60

CAGAGCAAGG   GAACCCAGGG   CAACAGGAGT   AGTTCACTCC   GCGAGAGGCC   GTCCACGAGA       120

CCCCCGCGCG   CAGCCATGAG   CCCCGCCCCC   CGCTGTTGCT   TGGAGAGGGG   CGGGACCTGG       180

AGAGAGGCTG   CTCCGTGACC   CCACC  ATG  TCC  TCT  CCT  ACC  ACG  AGT  TCC  CTG     232
                                Met  Ser  Ser  Pro  Thr  Thr  Ser  Ser  Leu
                                 1                   5

GAT  ACC  CCC  CTG  CCT  GGA  AAT  GGC  CCC  CCT  CAG  CCT  GGC  GCC  CCT  TCT   280
Asp  Thr  Pro  Leu  Pro  Gly  Asn  Gly  Pro  Pro  Gln  Pro  Gly  Ala  Pro  Ser
 10                  15                  20                  25

TCT  TCA  CCC  ACT  GTA  AAG  GAG  GAG  GGT  CCG  GAG  CCG  TGG  CCC  GGG  GGT   328
Ser  Ser  Pro  Thr  Val  Lys  Glu  Glu  Gly  Pro  Glu  Pro  Trp  Pro  Gly  Gly
               30                  35                  40

CCG  GAC  CCT  GAT  GTC  CCA  GGC  ACT  GAT  GAG  GCC  AGC  TCA  GCC  TGC  AGC   376
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| Pro | Asp | Pro | Asp | Val | Pro | Gly | Thr | Asp | Glu | Ala | Ser | Ser | Ala | Cys | Ser |     |
|     |     | 45  |     |     |     |     | 50  |     |     |     |     | 55  |     |     |     |     |
| ACA | GAC | TGG | GTC | ATC | CCA | GAT | CCC | GAA | GAG | GAA | CCA | GAG | CGC | AAG | CGA | 424 |
| Thr | Asp | Trp | Val | Ile | Pro | Asp | Pro | Glu | Glu | Glu | Pro | Glu | Arg | Lys | Arg |     |
|     |     | 60  |     |     |     |     | 65  |     |     |     |     | 70  |     |     |     |     |
| AAG | AAG | GGC | CCA | GCC | CCG | AAG | ATG | CTG | GGC | CAC | GAG | CTT | TGC | CGT | GTC | 472 |
| Lys | Lys | Gly | Pro | Ala | Pro | Lys | Met | Leu | Gly | His | Glu | Leu | Cys | Arg | Val |     |
|     | 75  |     |     |     |     | 80  |     |     |     |     | 85  |     |     |     |     |     |
| TGT | GGG | GAC | AAG | GCC | TCC | GGC | TTC | CAC | TAC | AAC | GTG | CTC | AGC | TGC | GAA | 520 |
| Cys | Gly | Asp | Lys | Ala | Ser | Gly | Phe | His | Tyr | Asn | Val | Leu | Ser | Cys | Glu |     |
| 90  |     |     |     |     | 95  |     |     |     |     | 100 |     |     |     |     | 105 |     |
| GGC | TGC | AAG | GGC | TTC | TTC | CGG | CGC | AGT | GTG | GTC | CGT | GGT | GGG | GCC | AGG | 568 |
| Gly | Cys | Lys | Gly | Phe | Phe | Arg | Arg | Ser | Val | Val | Arg | Gly | Gly | Ala | Arg |     |
|     |     |     |     | 110 |     |     |     |     | 115 |     |     |     |     | 120 |     |     |
| CGC | TAT | GCC | TGC | CGG | GGT | GGC | GGA | ACC | TGC | CAG | ATG | GAC | GCT | TTC | ATG | 616 |
| Arg | Tyr | Ala | Cys | Arg | Gly | Gly | Gly | Thr | Cys | Gln | Met | Asp | Ala | Phe | Met |     |
|     |     |     | 125 |     |     |     |     | 130 |     |     |     |     | 135 |     |     |     |
| CGG | CGC | AAG | TGC | CAG | CAG | TGC | CGG | CTG | CGC | AAG | TGC | AAG | GAG | GCA | GGG | 664 |
| Arg | Arg | Lys | Cys | Gln | Gln | Cys | Arg | Leu | Arg | Lys | Cys | Lys | Glu | Ala | Gly |     |
|     |     | 140 |     |     |     |     | 145 |     |     |     |     | 150 |     |     |     |     |
| ATG | AGG | GAG | CAG | TGC | GTC | CTT | TCT | GAA | GAA | CAG | ATC | CGG | AAG | AAG | AAG | 712 |
| Met | Arg | Glu | Gln | Cys | Val | Leu | Ser | Glu | Glu | Gln | Ile | Arg | Lys | Lys | Lys |     |
|     | 155 |     |     |     |     | 160 |     |     |     |     | 165 |     |     |     |     |     |
| ATT | CGG | AAA | CAG | CAG | CAG | CAG | GAG | TCA | CAG | TCA | CAG | TCG | CAG | TCA | CCT | 760 |
| Ile | Arg | Lys | Gln | Gln | Gln | Gln | Glu | Ser | Gln | Ser | Gln | Ser | Gln | Ser | Pro |     |
| 170 |     |     |     |     | 175 |     |     |     |     | 180 |     |     |     |     | 185 |     |
| GTG | GGG | CCG | CAG | GGC | AGC | AGC | AGC | TCA | GCC | TCT | GGG | CCT | GGG | GCT | TCC | 808 |
| Val | Gly | Pro | Gln | Gly | Ser | Ser | Ser | Ser | Ala | Ser | Gly | Pro | Gly | Ala | Ser |     |
|     |     |     |     | 190 |     |     |     |     | 195 |     |     |     |     | 200 |     |     |
| CCT | GGT | GGA | TCT | GAG | GCA | GGC | AGC | CAG | GGC | TCC | GGG | GAA | GGC | GAG | GGT | 856 |
| Pro | Gly | Gly | Ser | Glu | Ala | Gly | Ser | Gln | Gly | Ser | Gly | Glu | Gly | Glu | Gly |     |
|     |     |     | 205 |     |     |     |     | 210 |     |     |     |     | 215 |     |     |     |
| GTC | CAG | CTA | ACA | GCG | GCT | CAA | GAA | CTA | ATG | ATC | CAG | CAG | TTG | GTG | GCG | 904 |
| Val | Gln | Leu | Thr | Ala | Ala | Gln | Glu | Leu | Met | Ile | Gln | Gln | Leu | Val | Ala |     |
|     |     | 220 |     |     |     |     | 225 |     |     |     |     | 230 |     |     |     |     |
| GCC | CAA | CTG | CAG | TGC | AAC | AAA | CGC | TCC | TTC | TCC | GAC | CAG | CCC | AAA | GTC | 952 |
| Ala | Gln | Leu | Gln | Cys | Asn | Lys | Arg | Ser | Phe | Ser | Asp | Gln | Pro | Lys | Val |     |
|     | 235 |     |     |     |     | 240 |     |     |     |     | 245 |     |     |     |     |     |
| ACG | CCC | TGG | CCC | CTG | GGC | GCA | GAC | CCC | CAG | TCC | CGA | GAT | GCC | CGC | CAG | 1000 |
| Thr | Pro | Trp | Pro | Leu | Gly | Ala | Asp | Pro | Gln | Ser | Arg | Asp | Ala | Arg | Gln |     |
| 250 |     |     |     |     | 255 |     |     |     |     | 260 |     |     |     |     | 265 |     |
| CAA | CGC | TTT | GCC | CAC | TTC | ACG | GAG | CTG | GCC | ATC | ATC | TCA | GTC | CAG | GAG | 1048 |
| Gln | Arg | Phe | Ala | His | Phe | Thr | Glu | Leu | Ala | Ile | Ile | Ser | Val | Gln | Glu |     |
|     |     |     |     | 270 |     |     |     |     | 275 |     |     |     |     | 280 |     |     |
| ATC | GTG | GAC | TTC | GCT | AAG | CAA | GTG | CCT | GGT | TTC | CTG | CAG | CTG | GGC | CGG | 1096 |
| Ile | Val | Asp | Phe | Ala | Lys | Gln | Val | Pro | Gly | Phe | Leu | Gln | Leu | Gly | Arg |     |
|     |     |     | 285 |     |     |     |     | 290 |     |     |     |     | 295 |     |     |     |
| GAG | GAC | CAG | ATC | GCC | CTC | CTG | AAG | GCA | TCC | ACT | ATC | GAG | ATC | ATG | CTG | 1144 |
| Glu | Asp | Gln | Ile | Ala | Leu | Leu | Lys | Ala | Ser | Thr | Ile | Glu | Ile | Met | Leu |     |
|     |     | 300 |     |     |     |     | 305 |     |     |     |     | 310 |     |     |     |     |
| CTA | GAG | ACA | GCC | AGG | CGC | TAC | AAC | CAC | GAG | ACA | GAG | TGT | ATC | ACC | TTC | 1192 |
| Leu | Glu | Thr | Ala | Arg | Arg | Tyr | Asn | His | Glu | Thr | Glu | Cys | Ile | Thr | Phe |     |
|     | 315 |     |     |     |     | 320 |     |     |     |     | 325 |     |     |     |     |     |
| TTG | AAG | GAC | TTC | ACC | TAC | AGC | AAG | GAC | GAC | TTC | CAC | CGT | GCA | GGC | CTG | 1240 |
| Leu | Lys | Asp | Phe | Thr | Tyr | Ser | Lys | Asp | Asp | Phe | His | Arg | Ala | Gly | Leu |     |
| 330 |     |     |     |     | 335 |     |     |     |     | 340 |     |     |     |     | 345 |     |
| CAG | GTG | GAG | TTC | ATC | AAC | CCC | ATC | TTC | GAG | TTC | TCG | CGG | GCC | ATG | CGG | 1288 |
| Gln | Val | Glu | Phe | Ile | Asn | Pro | Ile | Phe | Glu | Phe | Ser | Arg | Ala | Met | Arg |     |
|     |     |     |     | 350 |     |     |     |     | 355 |     |     |     |     | 360 |     |     |
| CGG | CTG | GGC | CTG | GAC | GAC | GCT | GAG | TAC | GCC | CTG | CTC | ATC | GCC | ATC | AAC | 1336 |

|   |   |   |   |   |   |   |   |   |   |   |   |   |   |   |   |
|---|---|---|---|---|---|---|---|---|---|---|---|---|---|---|---|
| Arg | Leu | Gly | Leu | Asp | Asp | Ala | Glu | Tyr | Ala | Leu | Leu | Ile | Ala | Ile | Asn |
|   |   |   | 365 |   |   |   | 370 |   |   |   |   | 375 |   |   |   |

| ATC | TTC | TCG | GCC | GAC | CGG | CCC | AAC | GTG | CAG | GAG | CCG | GGC | CGC | GTG | GAG | 1384 |
|---|---|---|---|---|---|---|---|---|---|---|---|---|---|---|---|---|
| Ile | Phe | Ser | Ala | Asp | Arg | Pro | Asn | Val | Gln | Glu | Pro | Gly | Arg | Val | Glu |   |
|   |   | 380 |   |   |   |   | 385 |   |   |   |   | 390 |   |   |   |   |

| GCG | TTG | CAG | CAG | CCC | TAC | GTG | GAG | GCG | CTG | CTG | TCC | TAC | ACG | CGC | ATC | 1432 |
|---|---|---|---|---|---|---|---|---|---|---|---|---|---|---|---|---|
| Ala | Leu | Gln | Gln | Pro | Tyr | Val | Glu | Ala | Leu | Leu | Ser | Tyr | Thr | Arg | Ile |   |
|   | 395 |   |   |   |   | 400 |   |   |   |   | 405 |   |   |   |   |   |

| AAG | AGG | CCG | CAG | GAC | CAG | CTG | CGC | TTC | CCG | CGC | ATG | CTC | ATG | AAG | CTG | 1480 |
|---|---|---|---|---|---|---|---|---|---|---|---|---|---|---|---|---|
| Lys | Arg | Pro | Gln | Asp | Gln | Leu | Arg | Phe | Pro | Arg | Met | Leu | Met | Lys | Leu |   |
| 410 |   |   |   |   | 415 |   |   |   |   | 420 |   |   |   |   | 425 |   |

| GTG | AGC | CTG | CGC | ACG | CTG | AGC | TCT | GTG | CAC | TCG | GAG | CAG | GTC | TTC | GCC | 1528 |
|---|---|---|---|---|---|---|---|---|---|---|---|---|---|---|---|---|
| Val | Ser | Leu | Arg | Thr | Leu | Ser | Ser | Val | His | Ser | Glu | Gln | Val | Phe | Ala |   |
|   |   |   |   | 430 |   |   |   |   | 435 |   |   |   |   | 440 |   |   |

| TTG | CGG | CTC | CAG | GAC | AAG | AAG | CTG | CCG | CCT | CTG | CTG | TCG | GAG | ATC | TGG | 1576 |
|---|---|---|---|---|---|---|---|---|---|---|---|---|---|---|---|---|
| Leu | Arg | Leu | Gln | Asp | Lys | Lys | Leu | Pro | Pro | Leu | Leu | Ser | Glu | Ile | Trp |   |
|   |   |   | 445 |   |   |   |   | 450 |   |   |   |   | 455 |   |   |   |

| GAC | GTC | CAC | GAG | TGAGGGCTG | GCCACCCAGC | CCCACAGCCT | TGCCTGACCA | 1628 |
|---|---|---|---|---|---|---|---|---|
| Asp | Val | His | Glu |   |   |   |   |   |
|   |   | 460 |   |   |   |   |   |   |

| CCCTCCAGCA | GATAGACGCC | GGCACCCCTT | CCTCTTCCTA | GGGTGGAAGG | GGCCCTGGGC | 1688 |
|---|---|---|---|---|---|---|
| CGAGCCTGTA | GACCTATCGG | CTCTCATCCC | TTGGGATAAG | CCCCAGTCCA | GGTCCAGGAG | 1748 |
| GCTCCCTCCC | TGCCCAGCGA | GTCTTCCAGA | AGGGGTGAAA | GGGTTGCAGG | TCCCGACCAC | 1808 |
| TGACCCTTCC | CGGCTGCCCT | CCCTCCCCAG | CTTACACCTC | AAGCCCAGCA | CGCAGTGCAC | 1868 |
| CTTGAACAGA | GGGAGGGGAG | GACCCATGGC | TCTCCCCCCT | AGCCCGGGAG | ACCAGGGGCC | 1928 |
| TTCCTCTTCC | TCTGCTTTTA | TTTAATAAAA | ACTAAAAACA | GAAAAAAAAA | A | 1979 |

( 2 ) INFORMATION FOR SEQ ID NO: 2:

( i ) SEQUENCE CHARACTERISTICS:
        ( A ) LENGTH: 1688
        ( B ) TYPE: nucleic acid
        ( C ) STRANDEDNESS: double
        ( D ) TOPOLOGY: linear ( i i ) MOLECULE TYPE: cDNA to mRNA ( v i ) ORIGINAL SOURCE:
        ( A ) ORGANISM: Homosapiens ( x i ) SEQUENCE DESCRIPTION: SEQ ID NO: 2:

| TTTTGAGGGT | ATTTGAGTAG | CGGCGGTGTG | TCAGGGGCTA | AAGAGGAGGA | CGAAGAAAAG | 60 |
|---|---|---|---|---|---|---|
| CAGAGCAAGG | GAACCCAGGG | CAACAGGAGT | AGTTCACTCC | GCGAGAGGCC | GTCCACGAGA | 120 |
| CCCCCGCGCG | CAGCCATGAG | CCCCGCCCCC | CGCTGTTGCT | TGGAGAGGGG | CGGGACCTGG | 180 |

| AGAGAGGCTG | CTCCGTGACC | CCACC | ATG | TCC | TCT | CCT | ACC | ACG | AGT | TCC | CTG | 232 |
|---|---|---|---|---|---|---|---|---|---|---|---|---|
|   |   |   | Met | Ser | Ser | Pro | Thr | Thr | Ser | Ser | Leu |   |
|   |   |   | 1 |   |   | 5 |   |   |   |   |   |   |

| GAT | ACC | CCC | CTG | CCT | GGA | AAT | GGC | CCC | CCT | CAG | CCT | GGC | GCC | CCT | TCT | 280 |
|---|---|---|---|---|---|---|---|---|---|---|---|---|---|---|---|---|
| Asp | Thr | Pro | Leu | Pro | Gly | Asn | Gly | Pro | Pro | Gln | Pro | Gly | Ala | Pro | Ser |   |
| 10 |   |   |   |   | 15 |   |   |   |   | 20 |   |   |   |   | 25 |   |

| TCT | TCA | CCC | ACT | GTA | AAG | GAG | GAG | GGT | CCG | GAG | CCG | TGG | CCC | GGG | GGT | 328 |
|---|---|---|---|---|---|---|---|---|---|---|---|---|---|---|---|---|
| Ser | Ser | Pro | Thr | Val | Lys | Glu | Glu | Gly | Pro | Glu | Pro | Trp | Pro | Gly | Gly |   |
| 30 |   |   |   |   | 35 |   |   |   |   | 40 |   |   |   |   |   |   |

| CCG | GAC | CCT | GAT | GTC | CCA | GGC | ACT | GAT | GAG | GCC | AGC | TCA | GCC | TGC | AGC | 376 |
|---|---|---|---|---|---|---|---|---|---|---|---|---|---|---|---|---|
| Pro | Asp | Pro | Asp | Val | Pro | Gly | Thr | Asp | Glu | Ala | Ser | Ser | Ala | Cys | Ser |   |
| 45 |   |   |   |   | 50 |   |   |   |   | 55 |   |   |   |   |   |   |

| ACA | GAC | TGG | GGC | GTC | CTT | TCT | GAA | GAA | CAG | ATC | CGG | AAG | AAG | AAG | ATT | 424 |
|---|---|---|---|---|---|---|---|---|---|---|---|---|---|---|---|---|
| Thr | Asp | Trp | Gly | Val | Leu | Ser | Glu | Glu | Gln | Ile | Arg | Lys | Lys | Lys | Ile |   |
| 60 |   |   |   |   | 65 |   |   |   |   | 70 |   |   |   |   |   |   |

-continued

| | | | | | | | | | | | | | | | | |
|---|---|---|---|---|---|---|---|---|---|---|---|---|---|---|---|---|
| CGG | AAA | CAG | CAG | CAG | CAG | GAG | TCA | CAG | TCA | CAG | TCG | CAG | TCA | CCT | GTG | 472 |
| Arg 75 | Lys | Gln | Gln | Gln | Gln 80 | Glu | Ser | Gln | Ser 85 | Gln | Ser | Gln | Ser | Pro | Val | |
| GGG | CCG | CAG | GGC | AGC | AGC | AGC | TCA | GCC | TCT | GGG | CCT | GGG | GCT | TCC | CCT | 520 |
| Gly 90 | Pro | Gln | Gly | Ser 95 | Ser | Ser | Ser | Ala | Gly 100 | Pro | Gly | Ala | Ser | Pro 105 | | |
| GGT | GGA | TCT | GAG | GCA | GGC | AGC | CAG | GGC | TCC | GGG | GAA | GGC | GAG | GGT | GTC | 568 |
| Gly 110 | Gly | Ser | Glu | Ala | Gly 115 | Ser | Gln | Gly | Ser | Gly 120 | Glu | Gly | Glu | Gly | Val | |
| CAG | CTA | ACA | GCG | GCT | CAA | GAA | CTA | ATG | ATC | CAG | CAG | TTG | GTG | GCG | GCC | 616 |
| Gln 125 | Leu | Thr | Ala | Ala | Gln 130 | Glu | Leu | Met | Ile | Gln 135 | Gln | Leu | Val | Ala | Ala | |
| CAA | CTG | CAG | TGC | AAC | AAA | CGC | TCC | TTC | TCC | GAC | CAG | CCC | AAA | GTC | ACG | 664 |
| Gln 140 | Leu | Gln | Cys | Asn | Lys 145 | Arg | Ser | Phe | Ser | Asp 150 | Gln | Pro | Lys | Val | Thr | |
| CCC | TGG | CCC | CTG | GGC | GCA | GAC | CCC | CAG | TCC | CGA | GAT | GCC | CGC | CAG | CAA | 712 |
| Pro 155 | Trp | Pro | Leu | Gly | Ala 160 | Asp | Pro | Gln | Ser | Arg 165 | Asp | Ala | Arg | Gln | Gln | |
| CGC | TTT | GCC | CAC | TTC | ACG | GAG | CTG | GCC | ATC | ATC | TCA | GTC | CAG | GAG | ATC | 760 |
| Arg 170 | Phe | Ala | His | Phe | Thr 175 | Glu | Leu | Ala | Ile | Ile 180 | Ser | Val | Gln | Glu | Ile 185 | |
| GTG | GAC | TTC | GCT | AAG | CAA | GTG | CCT | GGT | TTC | CTG | CAG | CTG | GGC | CGG | GAG | 808 |
| Val 190 | Asp | Phe | Ala | Lys | Gln 195 | Val | Pro | Gly | Phe | Leu 200 | Gln | Leu | Gly | Arg | Glu | |
| GAC | CAG | ATC | GCC | CTC | CTG | AAG | GCA | TCC | ACT | ATC | GAG | ATC | ATG | CTG | CTA | 856 |
| Asp 205 | Gln | Ile | Ala | Leu | Leu 210 | Lys | Ala | Ser | Thr | Ile 215 | Glu | Ile | Met | Leu | Leu | |
| GAG | ACA | GCC | AGG | CGC | TAC | AAC | CAC | GAG | ACA | GAG | TGT | ATC | ACC | TTC | TTG | 904 |
| Glu 220 | Thr | Ala | Arg | Arg | Tyr 225 | Asn | His | Glu | Thr | Glu 230 | Cys | Ile | Thr | Phe | Leu | |
| AAG | GAC | TTC | ACC | TAC | AGC | AAG | GAC | GAC | TTC | CAC | CGT | GCA | GGC | CTG | CAG | 952 |
| Lys 235 | Asp | Phe | Thr | Tyr | Ser 240 | Lys | Asp | Asp | Phe | His 245 | Arg | Ala | Gly | Leu | Gln | |
| GTG | GAG | TTC | ATC | AAC | CCC | ATC | TTC | GAG | TTC | TCG | CGG | GCC | ATG | CGG | CGG | 1000 |
| Val 250 | Glu | Phe | Ile | Asn | Pro 255 | Ile | Phe | Glu | Phe | Ser 260 | Arg | Ala | Met | Arg | Arg 265 | |
| CTG | GGC | CTG | GAC | GAC | GCT | GAG | TAC | GCC | CTG | CTC | ATC | GCC | ATC | AAC | ATC | 1048 |
| Leu 270 | Gly | Leu | Asp | Asp | Ala 275 | Glu | Tyr | Ala | Leu | Leu 280 | Ile | Ala | Ile | Asn | Ile | |
| TTC | TCG | GCC | GAC | CGG | CCC | AAC | GTG | CAG | GAG | CCG | GGC | CGC | GTG | GAG | GCG | 1096 |
| Phe 285 | Ser | Ala | Asp | Arg | Pro 290 | Asn | Val | Gln | Glu | Pro 295 | Gly | Arg | Val | Glu | Ala | |
| TTG | CAG | CAG | CCC | TAC | GTG | GAG | GCG | CTG | CTG | TCC | TAC | ACG | CGC | ATC | AAG | 1144 |
| Leu 300 | Gln | Gln | Pro | Tyr | Val 305 | Glu | Ala | Leu | Leu | Ser 310 | Tyr | Thr | Arg | Ile | Lys | |
| AGG | CCG | CAG | GAC | CAG | CTG | CGC | TTC | CCG | CGC | ATG | CTC | ATG | AAG | CTG | GTG | 1192 |
| Arg 315 | Pro | Gln | Asp | Gln | Leu 320 | Arg | Phe | Pro | Arg | Met 325 | Leu | Met | Lys | Leu | Val | |
| AGC | CTG | CGC | ACG | CTG | AGC | TCT | GTG | CAC | TCG | GAG | CAG | GTC | TTC | GCC | TTG | 1240 |
| Ser 330 | Leu | Arg | Thr | Leu | Ser 335 | Ser | Val | His | Ser | Glu 340 | Gln | Val | Phe | Ala | Leu 345 | |
| CGG | CTC | CAG | GAC | AAG | AAG | CTG | CCG | CCT | CTG | CTG | TCG | GAG | ATC | TGG | GAC | 1288 |
| Arg 350 | Leu | Gln | Asp | Lys | Lys 355 | Leu | Pro | Pro | Leu | Leu 360 | Ser | Glu | Ile | Trp | Asp | |
| GTC | CAC | GAG | TGAGGGGCTG | | GCCACCCAGC | | CCCACAGCCT | | TGCCTGACCA | | | | | | | 1337 |
| Val | His | Glu 364 | | | | | | | | | | | | | | |

```
CCCTCCAGCA  GATAGACGCC  GGCACCCCTT  CCTCTTCCTA  GGGTGGAAGG  GGCCCTGGGC           1397

CGAGCCTGTA  GACCTATCGG  CTCTCATCCC  TTGGGATAAG  CCCCAGTCCA  GGTCCAGGAG           1457
```

-continued

| | | | | | |
|---|---|---|---|---|---|
| GCTCCCTCCC | TGCCCAGCGA | GTCTTCCAGA | AGGGGTGAAA | GGGTTGCAGG | TCCCGACCAC | 1517 |
| TGACCCTTCC | CGGCTGCCCT | CCCTCCCCAG | CTTACACCTC | AAGCCCAGCA | CGCAGTGCAC | 1577 |
| CTTGAACAGA | GGGAGGGGAG | GACCCATGGC | TCTCCCCCCT | AGCCCGGGAG | ACCAGGGGCC | 1637 |
| TTCCTCTTCC | TCTGCTTTTA | TTTAATAAAA | ACTAAAAACA | GAAAAAAAAA | A | 1688 |

(2) INFORMATION FOR SEQ ID NO: 3:

(i) SEQUENCE CHARACTERISTICS:
        (A) LENGTH: 31
        (B) TYPE: nucleic acid
        (C) STRANDEDNESS: single
        (D) TOPOLOGY: linear (ii) MOLECULE TYPE: another nucleic acid
        (synthetic DNA)

(xi) SEQUENCE DESCRIPTION: SEQ ID NO: 3:

GACGGATCCA TGTCCTCTCC TACCACGAGT T              31

(2) INFORMATION FOR SEQ ID NO: 4:

(i) SEQUENCE CHARACTERISTICS:
        (A) LENGTH: 29
        (B) TYPE: nucleic acid
        (C) STRANDEDNESS: single
        (D) TOPOLOGY: linear (ii) MOLECULE TYPE: another nucleic acid
        (synthetic DNA)

(xi) SEQUENCE DESCRIPTION: SEQ ID NO: 4:

CTAGAATTCG GAGGGTGGTC AGGCAAGGC              29

(2) INFORMATION FOR SEQ ID NO: 5:

(i) SEQUENCE CHARACTERISTICS:
        (A) LENGTH: 16
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

Asp Gln Pro Lys Val Thr Pro Trp Pro Leu Gly Ala Asp Pro Gln Ser
 1            5                  10               15

(2) INFORMATION FOR SEQ ID NO: 6:

(i) SEQUENCE CHARACTERISTICS:
        (A) LENGTH: 22
        (B) TYPE: nucleic acid
        (C) STRANDEDNESS: single
        (D) TOPOLOGY: linear (ii) MOLECULE TYPE: another nucleic acid
        (synthetic DNA)

(xi) SEQUENCE DESCRIPTION: SEQ ID NO: 6:

ATGTCCTCTC CTACCACGAG TT                      22

(2) INFORMATION FOR SEQ ID NO: 7:

(i) SEQUENCE CHARACTERISTICS:
        (A) LENGTH: 21
        (B) TYPE: nucleic acid
        (C) STRANDEDNESS: single
        (D) TOPOLOGY: linear (ii) MOLECULE TYPE: another nucleic acid
        (synthetic DNA)

(xi) SEQUENCE DESCRIPTION: SEQ ID NO: 7:

CCTCAGTGTC AGTGTCAGCG T                                                              21

( 2 ) INFORMATION FOR SEQ ID NO: 8:

( i ) SEQUENCE CHARACTERISTICS:
        ( A ) LENGTH: 26
        ( B ) TYPE: nucleic acid
        ( C ) STRANDEDNESS: single
        ( D ) TOPOLOGY: linear ( i i ) MOLECULE TYPE: another nucleic acid
            ( synthetic DNA )

( x i ) SEQUENCE DESCRIPTION: SEQ ID NO: 8:

CCGGAAGAAG AAGATTCGGA AACAGC                                                         26

( 2 ) INFORMATION FOR SEQ ID NO: 9:

( i ) SEQUENCE CHARACTERISTICS:
        ( A ) LENGTH: 19
        ( B ) TYPE: nucleic acid
        ( C ) STRANDEDNESS: single
        ( D ) TOPOLOGY: linear ( i i ) MOLECULE TYPE: another nucleic acid
            ( synthetic DNA )

( x i ) SEQUENCE DESCRIPTION: SEQ ID NO: 9:

GTGGCACGTC CGGACGTCC                                                                 19

( 2 ) INFORMATION FOR SEQ ID NO: 10:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) MOLECULE TYPE: another nucleic acid
            ( synthetic DNA )

( x i ) SEQUENCE DESCRIPTION: SEQ ID NO: 10:

ACCTACAGCA AGGACGACTT CC                                                             22

( 2 ) INFORMATION FOR SEQ ID NO: 11:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: another nucleic acid
            ( synthetic DNA )

( x i ) SEQUENCE DESCRIPTION: SEQ ID NO: 11:

CGGAACGGAC TGGTGGGAGG                                                                20